(12) United States Patent
Cresens

(10) Patent No.: US 7,903,839 B2
(45) Date of Patent: Mar. 8, 2011

(54) METHOD FOR CANCELING IMPACT OF PHYSICAL PROPERTY VARIABILITY ON IMAGE QUALITY PERFORMANCE OF DIGITAL IMAGING SYSTEM

(75) Inventor: Marc Cresens, Diest (BE)

(73) Assignee: Agfa HealthCare N.V., Mortsel (BE)

( * ) Notice: Subject to any disclaimer, the term of this patent is extended or adjusted under 35 U.S.C. 154(b) by 932 days.

(21) Appl. No.: 11/428,776

(22) Filed: Jul. 5, 2006

(65) Prior Publication Data

US 2007/0009096 A1    Jan. 11, 2007

Related U.S. Application Data

(60) Provisional application No. 60/699,684, filed on Jul. 15, 2005.

(30) Foreign Application Priority Data

Jul. 6, 2005  (EP) .................................... 05106112

(51) Int. Cl.
 *G06K 9/00*  (2006.01)
(52) U.S. Cl. ........................................ 382/100; 378/207

(58) Field of Classification Search ................. 382/100; 378/207

See application file for complete search history.

(56) References Cited

U.S. PATENT DOCUMENTS

| | | | | |
|---|---|---|---|---|
| 5,195,123 | A * | 3/1993 | Clement | 378/166 |
| 6,370,480 | B1 * | 4/2002 | Gupta et al. | 702/39 |
| 6,477,263 | B1 * | 11/2002 | Neri et al. | 382/137 |
| 6,694,047 | B1 | 2/2004 | Farrokhnia et al. | |
| 2003/0118227 | A1 * | 6/2003 | Winsor et al. | 382/132 |
| 2004/0245447 | A1 * | 12/2004 | Karasawa | 250/252.1 |

FOREIGN PATENT DOCUMENTS

| | | |
|---|---|---|
| EP | 1 484 015 A1 | 12/2004 |
| JP | 2004 223138 A | 8/2004 |

* cited by examiner

*Primary Examiner* — Wesley Tucker
*Assistant Examiner* — Mark Roz
(74) *Attorney, Agent, or Firm* — Houston Eliseeva LLP

(57) ABSTRACT

A method for canceling the impact of the physical property variability on the image quality performance of a digital imaging system, obtained during quality control (QC) analysis using a serial numbered quality control (QC) target by applying physical property deviation controlled behavior model corrections to the raw image quality performance. The serial numbered QC-target used for the QC analysis comprises target-specific, measured physical property data encoded in- or outside of QC-target.

15 Claims, 3 Drawing Sheets

METHOD FOR CANCELING IMPACT OF PHYSICAL PROPERTY VARIABILITY ON IMAGE QUALITY PERFORMANCE OF DIGITAL IMAGING SYSTEM

RELATED APPLICATIONS

This application claims the benefit under 35 USC 119(e) of U.S. Provisional Application No. 60/699,684, filed on Jul. 15, 2005, and claims priority to European Application No. 05106112.5, filed on Jul. 6, 2005, both of which are incorporated herein by reference in their entirety.

FIELD OF THE INVENTION

The present invention relates to image quality performance measurements of digital radiography systems. The invention more particularly relates to the cancellation of the impact of the variability of the physical properties of the quality control target used on the image quality performance results obtained during quality control testing in radiography systems.

BACKGROUND OF THE INVENTION

Image quality performance assessment (QA) and performance control (QC) for digital computed radiography systems (computed radiography CR or direct radiography DR) are of crucial importance within the context of medical diagnostic imaging. QA/QC testing and reporting of the results for digital X-ray projection image acquisition systems has globally evolved from a moral obligation status towards mandatory requirements, imposed by local health care regulations over the last decade.

Quality control can be performed at several instances during the life cycle of a digital radiography system. Manufacturers of digital computed radiography equipment can integrate image quality performance testing as part of their final QC-testing procedures, performed prior to customer shipment. Also, hospitals can perform acceptance testing. This acceptance testing relies on the results from image quality performance testing, executed after initial delivery, move, reconfiguration or repair of the image acquisition system or its vital components. Furthermore, periodic quality control testing, also referred to as constancy testing, can be part of a quality assurance program which tracks the image quality performance of computed radiography systems by reporting their time-consecutive QC-results, collected on a regular basis (daily, weekly, monthly, . . . ) to survey the system performance status relative to the image quality requirements and also to gather input for preventive maintenance scheduling.

As shown in FIG. 1 an image acquisition system for computed radiography is composed of various, linked subcomponents e.g., a console, a generator, an X-ray source, a dose monitor (optional) and a detector/digitizer.

The X-ray source is driven by the generator, receiving commands, settings and synchronization from the console. The generator settings, the tube assembly and the external filters, positioned in the beam-path near the X-ray tube, determine the energy spectrum of the generated photons used for projection imaging. An optional dose monitor inside the beam-path can provide accurate exposure information. An absorption shadow of an object (quality control target, patient), present in the optical path during exposure, is projected onto a X-ray sensitive detection surface, external to (storage phosphor medium based for CR) or integrated inside (solid state sensor based for DR) a digitizer. The digitizer converts the object's impinging X-ray shadow, captured and stored by the detector, into a digital image. Additional information, related to the image captured, such as: time, location, system configuration, system settings, imaging mode, exposure conditions, spectrum, dose, . . . , which can be relevant for routing, processing and storage of the generated image can be attached to the image data file. The obtained raw images, if used for medical purposes, are subject to dedicated diagnostic image processing to make them optimally suited for soft- or hardcopy inspection by radiologists or for computer aided detection purposes. The processed images can be visualized, archived, communicated, printed etc. on e.g., PACS systems.

The image quality performance testing of the image acquisition system, the front-end of the projection radiography imaging chain, performed during acceptance testing or constancy testing does not require X-ray exposure of human or animal beings.

Image quality performance testing involves acquisition and processing of digital images according to predetermined, well defined procedures and X-ray exposure conditions (sequence, timing, geometry, spectrum, dose, . . . ) by projection imaging one or multiple, dedicated quality control targets, also referred to as phantom objects, positioned in the beam-path between the X-ray source and the detection surface. These QC-targets can be composed of various objects and materials, pattern-wise arranged and spatially distributed inside the target such that the target is optimally suited as a test-object to produce images under exposure conditions, representative for the medical use of the equipment.

The obtained image data and the related information, contained inside the QC-target image, can be processed by dedicated QC-analysis software according to specific algorithms. These algorithms are designed to discriminate and measure the various, characteristic image quality performance parameters, representing the imaging capabilities of the system under test, and relate the calculated performance status to the required image quality criteria, proposed or mandatory for medical use. The QC-test results and comparative findings can be automatically reported and these reports can be archived in a PACS system or in a dedicated QC-document database (repository).

Since image acquisition systems for computed radiography are composed of various linked sub-components, the end-resulting image quality performance of the overall system will be determined by the individual image quality performance contributions of the various sub-components, part of the projection imaging chain. Image sharpness for instance, a typical important image quality performance parameter often analyzed, not only depends on the digitizer's modulation transfer function but is also influenced by the selected X-ray tube focus-size and by spatial blurring in the detector-plane. This spatial blurring can occur due to X-ray scatter inside the detector as a function of detector composition and photon spectrum or by strayed stimulation-light during plate-readout (CR).

For this reason, overall image quality performance testing often breaks up into multiple, separate QC-tests to evaluate the proper operation of the various system components, each executed under well-controlled geometry and exposure conditions according to predetermined and well-defined test procedures.

Since the QC-target, a prerequisite to create QC-target images, is an integral part of the image acquisition system during QC-testing, it will, like the other system-components that are part of the imaging chain, have an impact on the properties of the projected target-shadow, of which the QC-target image is generated and of which the image quality performance parameters are derived by calculations.

Image quality performance acceptance criteria are established by QC-analysis of QC-target images, captured from a nominal reference QC-target for each typical, representative system configuration under well-controlled exposure conditions. During these tests to establish the reference acceptance criteria for a given image acquisition system only system components showing nominal performance should be part of the imaging chain. These image quality performance acceptance criteria found can be used to evaluate the performance status of medical diagnostic image acquisition systems at the end of the manufacturing chain and out in the field.

Unlike the other system components, the QC-target is never part of the imaging chain during normal operation of the digital radiography equipment. By consequence QC-target physical property variability should not have any impact on the QC-test results since these should only reflect the real image quality, representative for system performance in normal, clinical use mode.

To ensure that these real QC-test results, for a given system at a given point in time, are independent of the QC-target having a specific serial number used, each QC-target manufactured should be a perfect duplicate of the nominal reference QC-target, used to determine the image quality performance acceptance criteria. However, due to tolerances and physical property variability of components used during QC-target assembly, there will always be an inevitable amount of uncertainty about the QC-test-results obtained if QC-target images are the basis for image quality performance evaluation of digital radiography systems.

To overcome the above mentioned problems a need exist to significantly reduce the impact of QC-target related tolerances and physical property variability on the performance results obtained during QA/QC-testing of digital radiography equipment.

SUMMARY OF THE INVENTION

The above-mentioned aspects are realized by the method for canceling the impact of the physical property variability of quality control (QC) target components on the image quality performance of a digital imaging system comprising obtaining image data for QC analysis using a serial numbered quality control target, calculating raw image quality performance, obtaining QC-target specific physical property data, obtaining behavior models for the image quality performance parameters under analysis, and obtaining image quality performance acceptance criteria, wherein the impact is calculated by applying physical property deviation controlled behavior model corrections to the raw image quality performance for comparison with the image quality performance acceptance criteria. Specific features for preferred embodiments of the invention are: the image data for QC analysis are obtained by X-ray exposure of a QC target in a computed radiography (CR) or direct radiography system (DR), the raw image quality performance is calculated using image quality analysis algorithms on relevant image data available within the QC-target image, the QC-target specific physical property data are available as patterns inside the QC-target image itself that can be detected, extracted and decoded by dedicated algorithms, the QC-target specific physical property data are available as hard- and/or software scannable and/or decodable patterns on a serial-number label adhered to the QC-target, the QC-target specific physical property data are available as hard- and/or software readable and decodable data stored in a non-volatile memory device attached in- or outside the QC-target, the QC-target specific physical property data linked to the QC-target serial number are available as data that are stored and that are accessible in an external, persisted repository, the behavior models include mathematical equations or statistically processed result-measurements performed with several type-identical QC-targets comprising materials with accurately measured physical properties, the image quality performance acceptance criteria are established for a nominal image acquisition system in combination with the reference QC-target, and further comprising creating a QC analysis report.

Further advantages and embodiments of the present invention will become apparent from the following description and drawings.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

According to the method of the present invention the impact of QC-target tolerances and physical property variability on the performance results obtained during QA/QC-testing of digital radiography equipment is reduced significantly. The performance results obtained according to this method are more reliable and better reflect the real image quality performance of the tested radiography system. Due to this higher reliability, narrower image quality performance margins and more stringent acceptance criteria can be used which leads to an improved image quality performance consistency. Also, QC-targets comprising X-ray absorbing materials with less stringent tolerances and physical property variability requirements can be used. This broadens the choice of available absorber materials suited for QC-target implementation and can reduce the cost of QC-target hardware. Furthermore, specialty materials with specific interesting properties but with less constant or with batch-wise fluctuating physical properties can therefore also be implemented in the QC-target.

Figure 1:
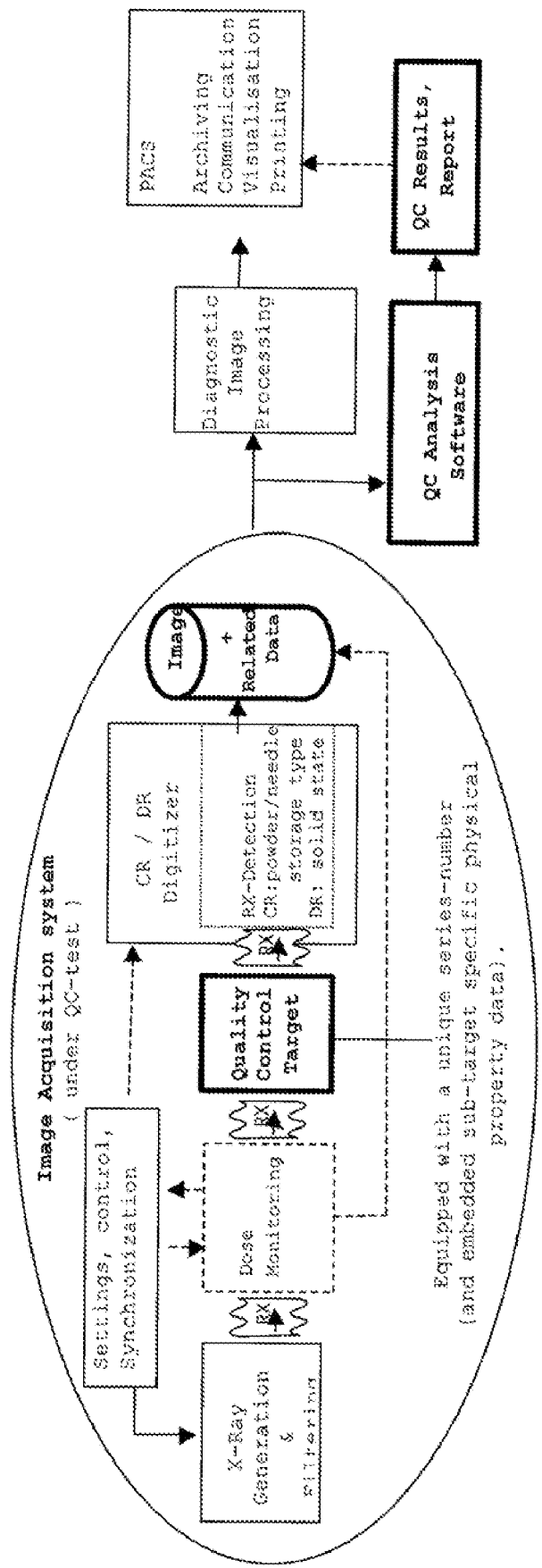
FIG. 1 shows a projection radiography CR/DR imaging chain.
Figure 2:
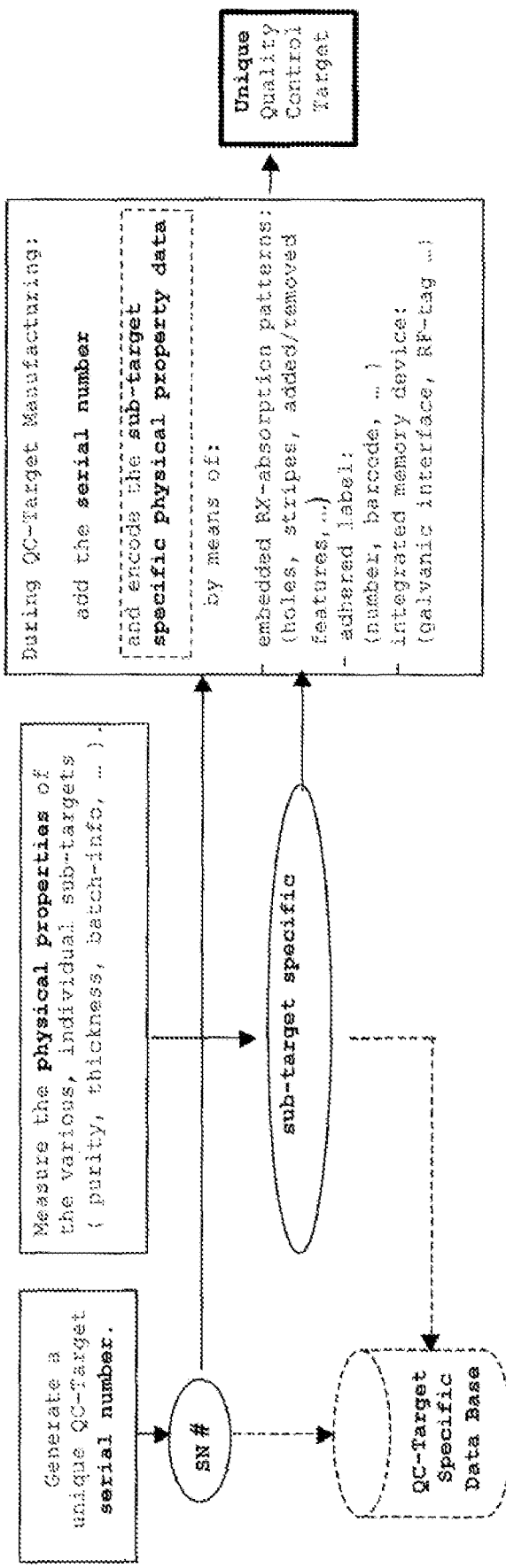
FIG. 2 shows the manufacturing flow for creating a unique quality control target.

According to the present invention as shown in FIG. 2 unique QC-targets are manufactured having a specific serial number and having encoded sub-target specific physical property data. Each individual, series-wise manufactured QC-target can physically differ more or less and in various ways from the reference QC-target (nominal QC-target), used to determine the reference image quality acceptance criteria. QC-targets can comprise various different embedded objects that can be pattern-wise arranged and distributed across the QC-target. The shape and geometry of these embedded objects can be important for the QC-analysis but also thickness, chemical composition and absorption properties can significantly influence the properties of the projected X-ray shadow, whereof the QC-target image is derived for QC-analysis.

Some of the physical differences in the embedded objects that are used in the QC-target can have a neglectable effect on the test results whereas other differences can have a much stronger impact on a single or on multiple image quality performance parameters that are being analyzed. Using these series-wise manufactured QC-targets as such for QC-testing will create a given level of inevitable uncertainty about the representativeness of the analysis-results obtained. It is an object of the present invention to reduce this level of result-uncertainty that is due to the fact that each QC-target manufactured is different in an unknown way.

As shown in FIG. 2 each QC target manufactured receives a unique, QC-target specific, serial number. The physical properties of the various, individual sub-targets, which will be incorporated in the QC-target during manufacturing, that are known upfront or that can be measured are incorporated in a data set. This set of QC-target specific physical property data can be composed of precisely measured thickness, length or shape data. Also individually or batch-wise analyzed purity or chemical composition data can be added. In fact, each sub-target related physical property aspect which can be monitored or is known upfront, can be useful to help reduce the QC-result uncertainty further down the QC-analysis process. This set of valuable, sub-target-specific physical property data is linked to the unique, QC-target specific serial number as an unbreakable information entity. This information entity can be added in- or outside the QC-target or can reside as persisted, accessible information inside a QC-target specific database or other type of data repository. The QC-target can be equipped with its unique, QC-target specific data using several techniques:

Hardcoding the QC-target specific data in- or outside the QC-target such that this information modulates the X-ray shadow during projection imaging. This way it will always be intimately coupled to the QC-target image. Possible techniques to physically encode this information entity in the QC-target are:
  removing QC-target material by computer numerical controlled machining, drilling, lasercutting, stripping. (For example by drilling holes in an X-ray absorbing layer);
  adding QC-target material by adhering dots or strips or by writing or printing patterns with X-ray absorbing ink;
  any other current or future technique able to modify the local absorption properties of the QC-target;
  Writing or printer-encoding the QC-target specific data along with the serial number on a label, adhered to the QC-target; and
  Storing the QC-target specific data in a non-volatile memory device, incorporated inside or adhered to the QC-target. Any current or future interface technology (galvanic, opto-coupled, electro-magnetic, magnetic, . . . ) can be used to communicate with the integrated memory device.

Finally, a unique QC-target is obtained which is linked to an accessible and non-volatile set of QC-target unique physical property data, stored in- or outside the QC-target.

Figure 3:
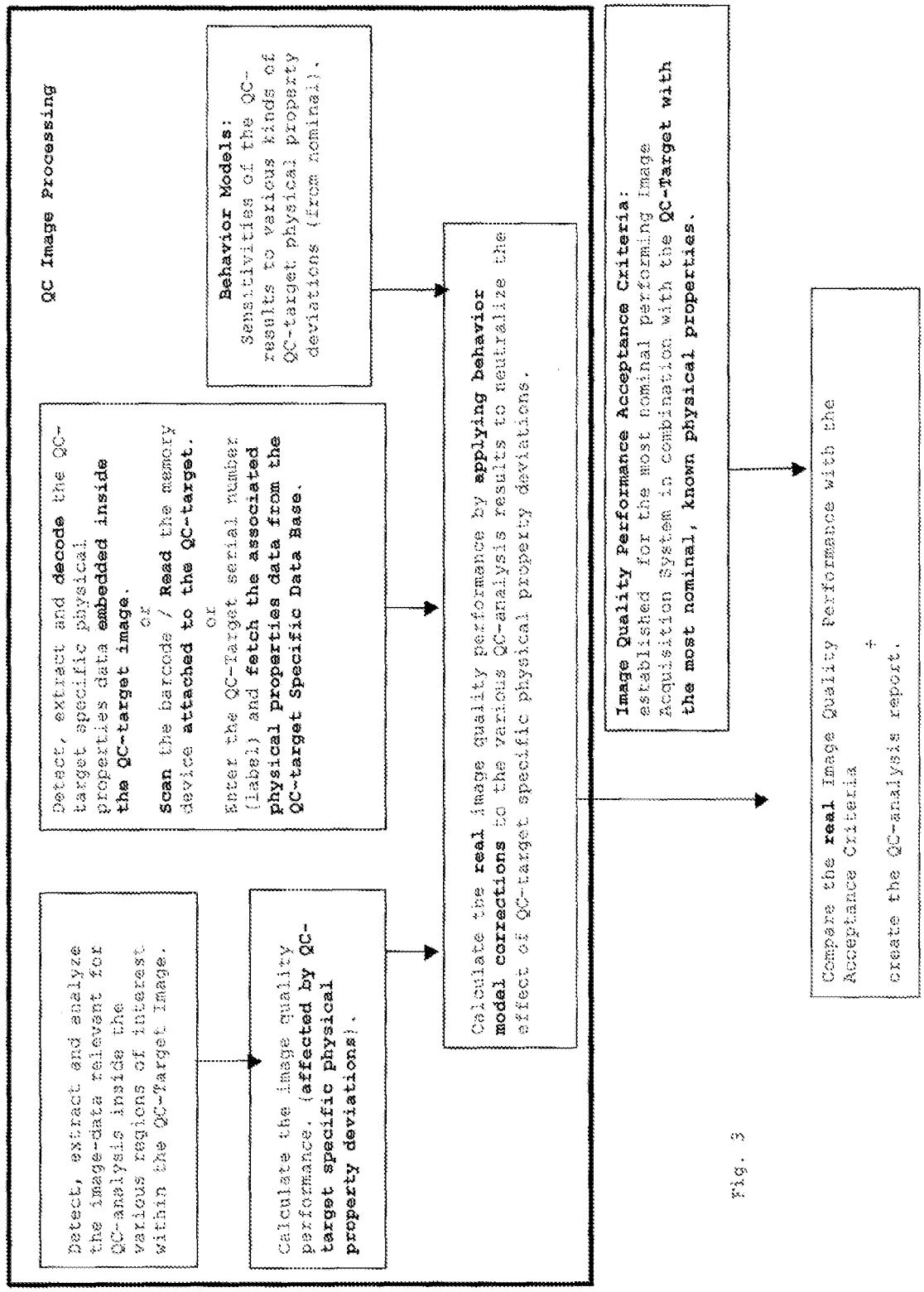
FIG. 3 shows the quality control image processing flow for obtaining the image quality performance results for a digital radiography system.

The obtained serial numbered QC-target can then be used for QC-analysis of digital projection radiography systems as shown in FIG. 3. Therefor, first a radiation image of the QC-target is obtained. Subsequently, the QC analysis software detects, extracts and analyses the image data available inside the various test-specific regions of interest within the QC-target image for QC-analysis calculations. Based on these image-data and using various dedicated, image quality analysis algorithms, the various, raw image quality performance parameters for the image acquisition system under test are calculated. These QC-results are achieved by analyzing QC-target images obtained from a specific, serial-numbered QC-target, which is not the nominal, unique reference QC-target. By consequence these raw performance results are affected by physical property variability between the unique, reference QC-target and the actual serial-numbered QC-target used. In a next step, dedicated QC image processing algorithms search for the QC-target specific physical property data, incorporated during manufacturing, and available now as valuable information entity.

Depending on the implementation given, this information can be available as:
  Detectable patterns inside the QC-target image itself. Dedicated algorithms can detect, extract and decode the information embedded in the QC-target image;
  Detectable patterns on the serial-number label adhered to the QC-target. The information present on the label can be scanned and decoded by dedicated hard- and/or software and handed over to the QC-analysis software;
  Data stored in a non-volatile memory device attached in- or outside the QC-target. The information stored in the memory device can be read and decoded by dedicated hard- and/or software and handed over to the QC-analysis software; and
  Data stored and accessible in an external, persisted repository (memory or database). The QC-target serial number can be scanned or read and entered. A data-link can be established with the external repository to import the associated physical properties data.

During product-research/development the behavior of the image quality performance parameters for analysis have been modeled for the various sources of physical property variability, associated with the materials and sub-targets used inside the QC-target. This set of behavior-models can consist of mathematical equations, linked to physics laws, or can, if dependencies are complex, rely on statistically processed result-measurements, performed with several type-identical QC-targets, comprising materials with accurately measured physical properties. The behavior-models reflect the sensitivities of the QC-results to various kinds of deviations of the serial-numbered QC-target physical properties relative to the reference values.

In the following step, based on three inputs:
  the raw image quality performance results calculated;
  the physical property deviations of the materials embedded in the QC-target used (relative to these of the nominal, reference QC-target); and,
  the behavior models;
the impact of QC-target specific variabilities on the QC-results calculated can be neutralized by computing result-corrections to more accurately assess the real image quality performance of the system under test. This is done by applying the behavior model corrections to the various QC-analysis raw results. The obtained, corrected, close to real image quality reflects the performance of the system as if it would have been QC-analyzed with the nominal QC-target rather than with the available, serial-numbered QC-target.

Furthermore for QA/QC-testing on digital radiography systems image quality performance acceptance criteria have also been established. These criteria have been established using the most nominal performing image acquisition system in combination with the reference QC-target, the QC-target with the most nominal, known, accurately measured physical properties.

In the next step, the QC analysis software will relate the physical property neutralized, close to real, image quality performance of the system under test with the image quality performance acceptance criteria, established for a nominal image acquisition system in combination with the reference QC-target. The results of this comparison between both the assessed and the reference performance are representative for the performance state of the equipment tested, and do not depend on the physical property deviations of the materials used inside the serial numbered QC-target available. A QC-analysis report, representing the image quality performance status of the system, can be automatically generated and archived.

While this invention has been particularly shown and described with references to preferred embodiments thereof, it will be understood by those skilled in the art that various changes in form and details may be made therein without departing from the scope of the invention encompassed by the appended claims.

What is claimed is:

1. Method for canceling the impact of the physical property variability of quality control targets on the image quality performance of a digital imaging system comprising:
   obtaining image data for quality control analysis of a first quality control target identified by a unique serial number;
   determining raw image quality performance parameters for the image data;
   obtaining quality control target specific physical property data for the first quality control target by reference to its unique serial number, the quality control target specific physical property data characterizing deviations in physical properties between the first quality control target and a second reference quality control target;
   obtaining behavior models for the image quality performance parameters under analysis;
   obtaining image quality performance acceptance criteria;
   generating physical property neutralized image quality performance parameters by correcting the raw image quality performance parameters using the behavior models and the quality control target specific physical property data to correct for differences between the first quality control target and the second reference quality control target;
   comparing the physical property neutralized image quality performance parameters to the image quality performance acceptance criteria to determine the image quality performance of the digital imaging system; and
   taking images of objects with the digital imaging system.

2. Method according to claim 1 wherein said image data for quality control analysis are obtained by X-ray exposure of the first quality control target in a computed radiography (CR) or direct radiography system (DR).

3. Method according to claim 1 wherein said raw image quality performance parameters are calculated using image quality analysis algorithms on relevant image data available within the image data of the first quality control target.

4. Method according to claim 1 wherein said quality control target specific physical property data are available as patterns inside the image data itself that are detected, extracted and decoded by dedicated algorithms.

5. Method according to claim 1 wherein said quality control target specific physical property data are available as hard- and/or software scannable and/or decodable patterns on a serial-number label adhered to the first quality control target.

6. Method according to claim 1 wherein said quality control target specific physical property data are available as hard- and/or software readable and decodable data stored in a non-volatile memory device attached in- or outside the first quality control target.

7. Method according to claim 1 wherein said quality control target specific physical property data are linked to the serial number and are available as data that are stored and that are accessible in an external, persistent repository.

8. Method according to claim 1 wherein said behavior models include mathematical equations or statistically processed result-measurements performed with several type-identical quality control targets comprising materials with measured physical properties.

9. Method according to claim 1 wherein said image quality performance acceptance criteria are established for a nominal image acquisition system in combination with the second reference quality control target.

10. Method according to claim 1 further comprising creating a quality control analysis report.

11. Method for canceling the impact of the physical property variability of quality control targets on the image quality performance of a digital imaging system comprising:
   obtaining image data for quality control analysis of a first quality control target;
   determining raw image quality performance parameters for the image data;
   obtaining quality control target specific physical property data for the first quality control target, the quality control target specific physical property data characterizing deviations in physical properties between the first quality control target and a second reference quality control target;
   obtaining behavior models for the image quality performance parameters under analysis;
   obtaining image quality performance acceptance criteria;
   generating physical property neutralized image quality performance parameters by correcting the raw image quality performance parameters using the behavior models and the quality control target specific physical property data to correct for differences between the first quality control target and the second reference quality control target;
   comparing the physical property neutralized image quality performance parameters to the image quality performance acceptance criteria to determine the image quality performance of the digital imaging system; and
   taking images of objects with the digital imaging system.

12. Method according to claim 11 wherein said image data for quality control analysis are obtained by X-ray exposure of the first quality control target in a computed radiography (CR) or direct radiography system (DR).

13. Method according to claim 11 wherein said raw image quality performance parameters are calculated using image quality analysis algorithms on relevant image data available within the image data of the first quality control target.

14. Method according to claim 11 wherein said quality control target specific physical property data are available as patterns inside the image data itself that are detected, extracted and decoded by dedicated algorithms.

15. Method according to claim 11 wherein said behavior models include mathematical equations or statistically processed result-measurements performed with several type-identical quality control targets comprising materials with measured physical properties.

* * * * *